United States Patent [19]

Hrib et al.

[11] Patent Number: 5,143,923
[45] Date of Patent: Sep. 1, 1992

[54] BENZOISOTHIAZOLE- AND BENZIOSOXAZOLE-3-CARBOXAMIDES

[75] Inventors: Nicholas J. Hrib, Somerville; John G. Jurcak, Union City, both of N.J.

[73] Assignee: Hoechst-Roussel Pharmaceuticals Inc., Somerville, N.J.

[21] Appl. No.: 693,168

[22] Filed: Apr. 29, 1991

[51] Int. Cl.⁵ .................. A61K 31/445; C07D 413/10; C07D 417/10
[52] U.S. Cl. .................. 514/321; 514/256; 514/269; 514/322; 514/323; 514/324; 544/298; 544/333; 546/198; 546/199
[58] Field of Search ............... 544/298, 333; 546/198, 546/199; 514/256, 269, 321, 322, 324, 323

[56] References Cited

U.S. PATENT DOCUMENTS

| | | | |
|---|---|---|---|
| 3,145,215 | 8/1964 | Kirchner | 548/370 |
| 3,576,810 | 4/1971 | Duncan | 546/226 |
| 4,021,552 | 5/1977 | Welstead | 544/38 |
| 4,327,103 | 4/1982 | Helsley | 546/201 |
| 4,452,799 | 6/1984 | Temple | 544/230 |
| 4,710,500 | 12/1987 | Perregaard | 544/364 |
| 4,758,503 | 7/1988 | Sato | 430/543 |

FOREIGN PATENT DOCUMENTS

| | | |
|---|---|---|
| 0138280 | 4/1985 | European Pat. Off. |
| 0200444 | 11/1986 | European Pat. Off. |
| 0261964 | 3/1988 | European Pat. Off. |
| 0294292 | 12/1988 | European Pat. Off. |
| 0343961 | 11/1989 | European Pat. Off. |
| 3827253 | 3/1989 | Fed. Rep. of Germany |
| 2169292 | 7/1986 | United Kingdom |

OTHER PUBLICATIONS

U.S. Patent Application Ser. No. 639,639 filed Jan. 10, 1991.
L. Amoretti, et al., Il Farmaco (Ed. Sc.), 27, 855 (1972).
E. Molina, et al., Acta Bio-Med., 45, 183 (1974).
J. P. Yevich, J. Med. Chem., 29, 359 (1986).
J. T. Strupczewski, et al., J. Med. Chem., 28, 761 (1985).

*Primary Examiner*—Cecilia Tsang
*Attorney, Agent, or Firm*—Raymond R. Wittekind

[57] ABSTRACT

Novel benzisothiazole- and benzisoxazole-3-carboxamides, processes and intermediates for the preparation thereof, and methods of treating psychoses utilizing compounds and compositions thereof are disclosed.

21 Claims, No Drawings

BENZOISOTHIAZOLE- AND BENZIOSOXAZOLE-3-CARBOXAMIDES

DESCRIPTION OF THE INVENTION

The present invention relates to novel benzisothiazole- and benzisoxazole-3-carboxamides. More particularly, the present invention relates to benzisothiazole- and benzisoxazole-3-carboxamides of the formula

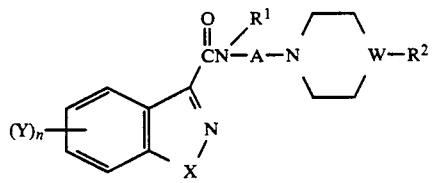

wherein $R^1$ is hydrogen or loweralkyl; $R^2$ is loweralkyl, or a group of the formula

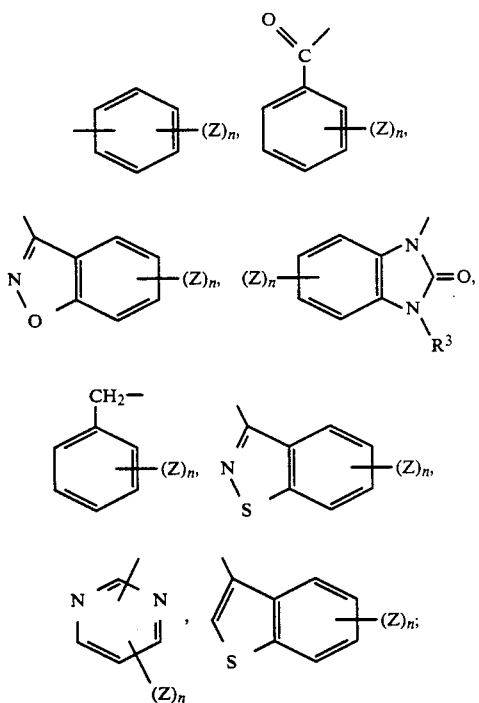

$R^3$ is hydrogen or loweralkyl; A is loweralkylene, a group of the formula —$CHR^4CH=CHCHR^4$—, or —$CHR^4\equiv CHR^4$—; $R^4$ is hydrogen or loweralkyl; X is O or S; W is N or CH; Y is hydrogen, loweralkyl, loweralkoxy, hydroxy, halogen, or trifluoromethyl; Z is hydrogen, loweralkyl, loweralkoxy, hydroxy, halogen, or trifluoromethyl; n is 1 or 2; wherein the solid line (—) refers to the point of attachment of the group to the indicated member of the formula; the geometric and optical isomers thereof; or a pharmaceutically acceptable salt thereof, useful for the treatment of psychoses, alone or in combination with inert adjuvants.

Subgeneric to the benzisothiazole- and benzisoxazoles-3-carboxamides of the present invention are those compounds wherein:

a. $R^2$ is a group of the formula

-continued

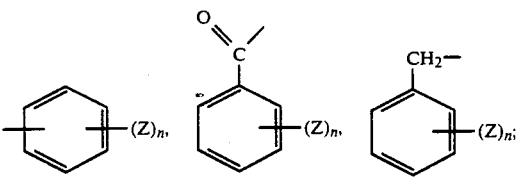

b. $R^2$ is

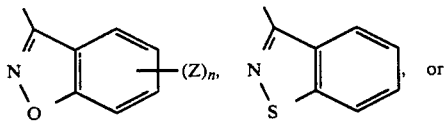

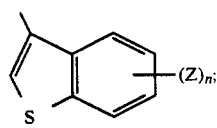

c. $R^2$ is

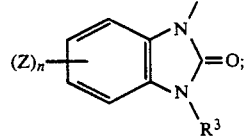

and d. $R^2$ is

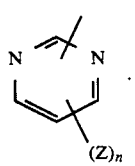

As used through the specification and appended claims, the term "alkyl" refers to a straight or branched chain hydrocarbon radical containing no unsaturation and having 1 to 7 carbon atoms such as methyl, ethyl, 1-propyl, 2-propyl, 1-butyl, 1-pentyl, 2-pentyl, 3-hexyl, 4-heptyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy and the like; the term "halogen" refers to a member of a family consisting of chlorine, fluorine, bromine, or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diastereomeric salts of those instant compounds characterized by the presence of a basic amino group and optically active acid, or by the synthesis from optically active precursors.

The present invention comprehends all optical isomers and racemic forms thereof. The formulas of the compounds shown herein are intended to encompass all possible optical isomers of the compounds so depicted.

The designations "E" and "Z" refer to the arrangement of the substituents bound to the carbon-to-carbon double bond of the 1-piperazinyl-2-butenes of the present invention. In the butenes designated "E", the hydrogen atoms are on opposite sides of the double bond, i.e., trans to each other. In the butenes designated "Z", the hydrogen atoms are on the same side of the double bond, i.e., cis to each other.

The benzisothiazoles- and benzisoxazole-3-carboxamides of the present invention are preferably prepared by alkylating a haloalkylamide of formula 1

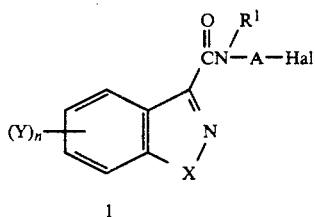

1 wherein $R^1$, A, Y, X, and n are as hereinbeforedescribed and Hal is chloro, bromo, or iodo with a secondary amine of formula 2

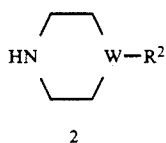

2 wherein $R^2$ and W are as hereinbeforedescribed at an elevated temperature within the range of about 50° to about 200° C., most perferably at a temperature within the range of about 120° to about 190° C. in N-methylpyrrolidone, a dipolar aprotic solvent. In addition to N-methylpyrrolidone, other dipolar aprotic solvents such as, for example, dimethylacetamide, dimethylformamide, hexamethylphosphoramide, and dimethylsulfoxide at a condensation temperature sufficient to assure a reasonable rate of reaction within the temperature range compatible with the solvent may be employed.

A base such as, for example, as alkali metal or alkaline earth carbonate or bicarbonate, i.e., lithium, sodium, or potassium carbonate or bicarbonate may be employed alone, or together with an alkylation promoter such as, for example, an alkali metal iodide, i.e., lithium, sodium, or potassium iodide. Potassium carbonate and sodium iodide are, respectively, the preferred base and condensation promoter.

When a base and an alkylation promoter are employed to effect the alkylation, acetonitrile may be used as the solvent, the alkylation being conducted at a temperature within the range of about 50° C. to the reflux temperature of the reaction medium, a alkylation temperature within the range of about 75° C. to the reflux temperature being preferred.

Alternatively, the benzisothiazole- and benzisoxazole-3-carboxamides of the present invention are prepared by condensing an acid halide of formula 3

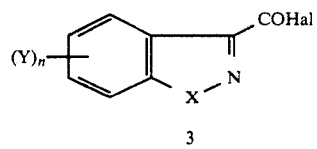

3 wherein X, Y, and n are as hereinbeforedescribed and Hal is chloro or bromo with a heterocyclic amine of formula 2a

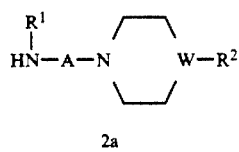

2a wherein $R^1$, $R^2$, A, and W are as above in the presence of an acid acceptor, for example, a tertiary amine such as trialkylamine, i.e., trimethylamine, triethylamine, or tri-n-propylamine, or a heterocyclic amine, i.e., pyridine, picoline, lutidine, or collidine, in a suitable solvent. Among suitable solvents are halocarbons, for example, dichloromethane, trichloromethane, and 1,1- and 1,2-dichloroethane, dichloromethane being preferred, and aromatic solvents, for example, benzene, toluene, and xylene, toluene being preferred. Trialkylamines are the preferred acid acceptors. Triethyl amine is the most preferred acceptor.

The benzisothiazole- and benzisoxazole-3-carboxamides of the present invention are also prepared by aminating a benzisothiazole- or benzisoxazole-3-carboxylic acid ester of formula 4

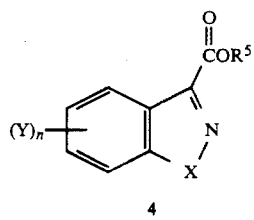

4 wherein $R^5$ is alkyl and X, Y, and n are as hereinbeforedescribed with an aminoalkane of formula 5

5 wherein A and $R^1$ are as above to provide a hydroxylalkylaminecarboxamide of formula 6.

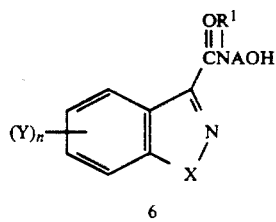

6 which is converted to a benzisothiazole- and benzisoxazole-carboxamides of the present invention. The amination is performed in an aromatic solvent such as, for example, benzene, toluene, xylene, or mesitylene, or an alcohol such as, for example, ethanol, 2-propanol, or 1-butanol, at a temperature from about 100° to about 140° C. Toluene is the preferred solvent. When an elevated reaction temperature is employed, the amination is preferably carried out in a pressure reaction vessel.

The conversion of a hydroxyalkylaminocarboxamide 6 to an ultimate benzisothiazole- or benzisoxazole is accomplished by treating a hydroxyalkylcarboxamide 6 with a sulfonyl chloride of formula 7

$$R^6SO_2Hal$$

7 wherein $R^6$ is alkyl, phenyl, or tolyl, and Hal is chloro or bromo in the presence of an acid acceptor, for example, a trialkylamine such as triethylamine in an aromatic solvent, for example, benzene, toluene, or xylene at a reaction temperature of about 0° to about 25° C. to form a sulfonate 8 of a hydroxyalkylcarboxamide 6

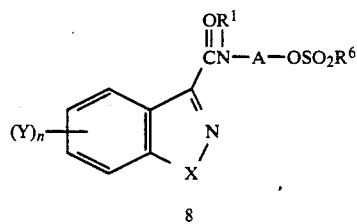

8 wherein A, $R^1$, $R^6$, X, Y, and n are as hereinbeforedescribed, which is treated, preferably without isolation, with a piperidine or piperazine 2, neat or dissolved in an ethereal solvent such as 1,2-dimethoxyethane, 2-methoxyethyl ether, tetrahydrofuran, or dioxane at a reaction temperature of about 25° C. to the reflux temperature of the reaction medium. Tetrahydrofuran is the preferred ethereal solvent. The reflux temperature is the preferred reaction temperature.

A cosolvent such as tetrahydrofuran may be used in the sulfonation step.

Preferred sulfonating agents 7 are alkylsulfonylchlorides, methanesulfonyl chloride being most preferred.

The following N-(hydroxyalkyl)benzisoxazole- and benzisothiazole-3-carboxamide sulfonates were prepared in situ as intermediates for the preparation of the ultimate benzisothiazole- and benzisoxazole-3-carboxamides.

a. N-methyl-N-(2-hydroxyethyl)-1,2-benzisothiazole-3-carboxamide methanesulfonate;
b. N-methyl-N-(2-hydroxyethyl)-1,2-benzisoxazole-3-carboxamide methanesulfonate;
c. N-(1-methylethyl)-N-(2-hydroxyethyl)-1,2-benzisoxazole-3-carboxamide methanesulfonate; and
d. N-(1-methylethyl)-N-(3-hydroxypropyl)-1,2-benzisoxazole-3-carboxamide methanesulfonate, The starting materials and substrates of the processes for the synthesis of the benzisothiazole- and benzisoxazole-3-carboxamides of the present invention are either commercially available or preparable by methods well-known in the art. For example, 3-halocarbonylbenzisothiazoles 3 and 3-(haloalkylaminocarbonylbenzisothiazoles 1 are prepared by the processes described in L. Amoretti, et al., IlFarmaco (Ed. Sc.), 27, 855 (1972).

The corresponding benzisoxazoles, i.e., the starting materials of formulas 1 and 3 wherein X is O, are prepared by adaptation of the procedures described by L. Amoretti, et al., id., at 859 to 861, or by those disclosed by K. Sato and H. Hiraiin U.S. Pat. No. 4,758,503 granted on Jul. 19, 1988.

Specifically, a 3-(haloalkylaminocarbonylbenzisothiazole or -benzisoxazole 11 wherein $R^1$ is methyl, A is alkyl of 2 to 4 and X, Y, Hal, and n are as described above is prepared by alkylating a benzoisothiazole- or benzisoxazole-3-carboxamide 9 wherein $R^1$ is methyl and X, Y, and n are as described hereinbefore with a dihaloalkane 10 of the formula HalAHal wherein A and Halo are as before described in the presence of an alkali metal hydride (e.g., sodium hydride or an oil dispersion thereof) in a dipolar aprotic solvent (e.g., dimethylformamide) at a reaction temperature within the range of about 0° to about 25° C.

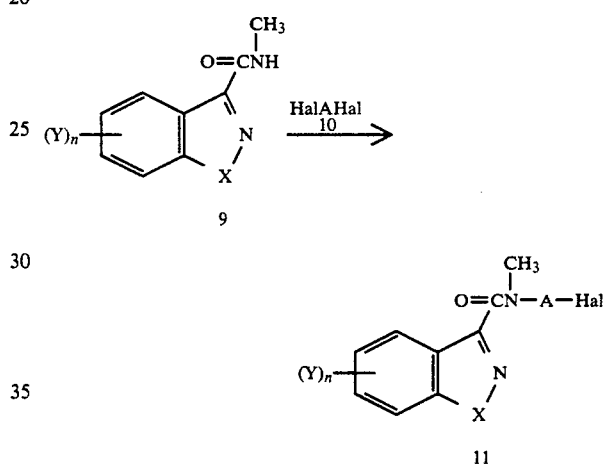

The reactants are generally available from commercial sources described in the art, or preparable by conventional methods, thus, for example, 4-(4-fluorobenzoyl)piperidine, the reactant for the fabrication of the present benzisothiazole- and benzisoxazole-3-carboxamides wherein $R^2$ is

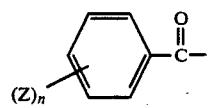

and W is CH is described in U.S. Pat. No. 3,576,810 issued Apr. 27, 1971, 4-(6-chloro-1,2-benzisoxazol-3-yl)piperidine, the substrate for the preparation of the ultimate compounds of the present invention, i.e., those compounds wherein $R^2$ is

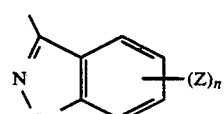

and W is CH is reported in U.S. Pat. No. 4,327,103 issued Apr. 27, 1982, and 4-(benzisothiazol-3-yl)piperazines, e.g., piperazine substrates for the synthesis of the carboxamides wherein $R^2$ is

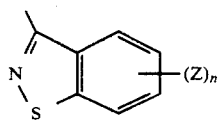

and W is H are disclosed in U.S. Pat. No. 4,452,799 issued Jun. 5, 1984.

The reactants necessary for the construction of benzisothiazole- and benzisoxazole-3-carboxamides wherein A is —CH$_2$CH=CHCH$_2$— or —CH$_2$C≡CCH$_2$—, i.e., amines of the formula

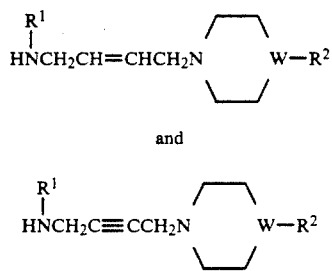

wherein R$^1$, R$^2$, W and m are as hereinbeforedescribed, are mentioned in U.S. Patent Ser. No. 07/639,639.

The benzoisothiazole- and benzisoxazole-3-carboxamides of the present invention are useful for treating psychoses by virtue of their ability to block apomorphine-induced climbing in mammals.

Antipsychotic activity is determined in the climbing mice assay by methods similar to those described by P. Protais et al., Psychopharmacol., 50, 1 (1976) and B. Costal, Eur. J. Pharmacol., 50, 39 (1978).

The subject CK-1 male mice (23–27 grams) are group-housed under standard laboratory conditions. The mice are individually placed in wire mesh stick cages (4"×4"10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior | Score |
|---|---|
| Mice with: | |
| 4 paws on bottom (no climbing) | 0 |
| 2 paws on the wall (rearing) | 1 |
| 4 paws on the wall (full climb) | 2 |

Mice consistently climbing before the injection of apormorphine are discarded.

With full-developed apomorphine climbing, the animals are hanging onto the cage walls, rather motionless, over longer periods of time. By contrast, climbs due to mere motor stimulation usually only last a few seconds.

The climbing scores are individually totaled (maximal score; 6 per mouse over 3 readings) and the total score of the control group (vehicle intraperitioneally-apomorphine subcutaneously) is set to 100%. ED$_{50}$ values with 95% confidence limits are calculated by a Linear Regression Analysis. Antipsychotic activity expressed as the ED$_{50}$ value of representative benzisothiazole- and benzisoxazole-3-carboxamides as well as two standard antipsychotics are presented in Table I.

TABLE I

| Compound | Antipsychotic Activity ED$_{50}$ (mg/kg) |
|---|---|
| N-[2-(1-(2-methoxyphenyl)-4-piperazinyl)ethyl]-1,2-benzisothiazole-3-carboxamide | 6.3 |
| N-[4-(1-(1,2-benzisothiazol-3-yl)-4-piperazinyl)butyl]-1,2-benzisothiazole-3-carboxamide | 8.3 |
| N-methyl-N-[4-(1-(2-methoxyphenyl)-4-piperazinyl)butyl]-1,2-benzisothiazole-3-carboxamide | 4.2 |
| N-methyl-N-[4-(1-(2-methoxyphenyl)-4-piperazinyl)butyl-1,2-benzisothiazole-3-carboxamide | 9.6 |
| N-methyl-N-[4-(1-(6-fluorobenzo[b]-thiophen-3-yl)-4-piperazinyl)butyl]-1,2-benzisothiazol-3-carboxamide | 4.5 |
| N-[2-(1-(6-fluorobenzo[b]-thiophen-3-yl)-4-piperazinyl)-ethyl-1,2-benzisoxazole-3-carboxamide | 4.9 |
| N-methyl-N-[4-(1-(6-fluoro-1,2-benzisoxazol-3-yl))-4-piperidinyl)-butyl]-1,2-benzisothiazole-3-carboxamide | 1.5 |
| N-[2-(1-(4-fluorobenzoyl)-4-piperidinyl)ethyl]1,2-benzisothiazole-3-carboxamide | 3.6 |
| N-methyl-N-[4-(1-6-fluorobenzo[b]thiophen-3-yl)-4-piperazinyl)butyl]-1,2-benzisoxazole-3-carboxamide | 5.0 |
| Haloperidol (Standard) | 0.11 |
| Sulpiride (Standard) | 4.5 |

Antipsychotic activity is achieved when the present benzoisothiazole- and benzisoxazole-3-carboxamides are administered to a subject requiring such treatment as effective oral, parenteral or intravenous dose of from 0.01 to 50 mg/kg of body weight per day. A particularly preferred effective range is about 25 mg/kg of body weight per day. It is to be understood, however, that for any particular subject, specific dosage regimens should be adjusted to the individual need and the professional judgment of the person administering or supervising the administration of the aforesaid compound. It is to be further understood that the dosages set forth herein are exemplary only and they do not, to any extent, limit the scope or practice of the invention.

The antipsychotic profile of the present benzisothiazole- and benzisoxazole-3-carboxamides is enhanced as a result of their unexpectedly low propersity to cause undesirable extra pyramidal side effects. Potential for undersible extrapyramidal side effect activity is determined in the inhibition of apormorphine stereotypy assay by methods similar to those described by N. E. Anden, et al., J. Pharma. Pharmacol., 19, 627, (1967) and A. M. Ernst, et al., Psychopharmacologia (Berl.), 10, 316, (1967).

In this assay, groups of male Wistar rats (125–200 grams) are used and food and water are available ad libitum. Drugs are prepared using distilled water and, if insoluble, a suitable surfactant is added. The route of administration may be varied and the dosage volume is 10 ml/kg. For a primary screen, a group size of six is used. Drug is administered one hour prior to scoring and the animals are placed in individual clear plastic cages (24×14×13 cm). The control group receives vehicle. Apomorphine hydrochloride solution is prepared at a concentration of 15 mg/10 ml in a 0.03% ascorbic acid stock solution (30 mg of ascorbic acid in 100 ml of 1% saline) to increase the stability of the apomorphine hydrochloride while in solution. Apomorphine hydrochloride solution is administered at a dose of 1.5 mg/kg subcutaneous (s.c.) with a dosage volume of 1 ml/kg. Fifty minutes after drug dosing, stereotypic behavior is noted. Stereotypic activity is defined as sniffing, licking or chewing behavior that occurs in a repetitive manner and is rated as follows: Constant sniffing, licking or chewing without interruption; the animal is considered protected if this behavior is interrupted.

The percent effectiveness of a drug is determined by the number of animals protected in each group. Antipsychotics displaying little effect in this assay would be expected to show a low propensity to cause undesirable extrapyramidal side effects and/or tardive dyskinesias in mammals. (N. C. Moore and S. Gershon, Clinical Neuropharmacology, 12, 167, (1989).

A dose-response is run in the same manner as a primary screen except that a group size of 10 is used and the animals are dosed in a randomized manner. One group receives vehicle. $ED_{50}$ for stereotypy are calculated by means of probit analysis.

Inhibition of apomorphine induced sterotypy of representative benzisothiazole-and benzisoazole-3-carboxamides of the present invention and two standards is given in Table II.

TABLE II

| Compounds | Dose (mg/kg) body wt.) | % Inhibition of apomorphine induced stereotypy |
|---|---|---|
| N-[2-(1-(2-methoxyphenyl-4-piperazinyl)ethyl]-1,2-benzisothiazole-3-carboxamide | 51.8 | 50 |
| N-[4-(1-(1,2-benzisothiazol-3-yl)-4-piperazinyl)butyl]-1,2-benzisothiazole-3-carboxamide | 40 | 17 |
| N-methyl-N-[4-(1-(2-methoxyphenyl)-4-piperazinyl)butyl]-1,2-benzisothiazole-3-carboxamide | 39.2 | 50 |
| N-methyl-N-[4-(1-(1,2-benzisothiazol-3-yl)-4-piperazinyl)butyl-1,2-benzisothiazole-3-carboxamide | 40 | 100 |
| N-methyl-N-[4-(1-(6-fluorobenzo[b]thiophen-3-yl)-4-piperazinyl)butyl]-1,2-benzisothiazol-3-carboxamide | 40 | 100 |
| N-[2-(1-(6-fluorobenzo[b]thiophen-3-yl)-4-piperazinyl)ethyl-1,2-benzisoxazole-3-carboxamide | 80 | 0 |
| N-methyl-N-[4-(1-(6-fluoro-1,2-benzisoxazol-3-yl)-4-piperidinyl)butyl]-1,2-benzisothiazole-3-carboxamide | 20 | 100 |
| N-[2-(1-(4-fluorobenzoyl)-4-piperidinyl)ethyl] 1,2-benzisothiazole-3-carboxamide | 20 | 67 |
| N-methyl-N-[4-(1-(6-fluoro- | 52 | 50 |

TABLE II-continued

| Compounds | Dose (mg/kg) body wt.) | % Inhibition of apomorphine induced stereotypy |
|---|---|---|
| benzo[b]thiophen-3-yl)-4-piperazinyl)butyl]-1,2-benzisoxazole-3-carboxamide | | |
| haloperidol (standard) | 0.2 | 50 |
| thioridazine (standard) | 16 | 50 |

Compounds of the invention include:

a. N-[2-((1-methyl)-4-piperazinyl)ethyl]-6-methyl-1,2-benzisothiazole-3-carboxamide;
b. 5-methoxy-N-[2-((1-methyl)-4-piperazinyl)ethyl]-1,2-benzisothiazole-3-carboxamide;
c. 5-hydroxy-N-[2-((1-methyl)-4-piperazinyl)ethyl]-1,2-benzisothiazole-3-carboxamide;
d. 7-chloro-N-[2-((1-methyl)-4-piperazinyl)ethyl]-1,2-benzisothiazole-3-carboxamide;
e. N-[2-((1-methyl)-4-piperazinyl)ethyl]-6-trifluoromethyl-1,2-benzisothiazole-3-carboxamide;
f. 6,7-dichloro-N-[2-((1-methyl)-4-piperazinyl)ethyl]-6-methyl-1,2-benzisothiazole-3-carboxamide;
g. N-{2-[1-(3-methylbenzyl)]-4-piperazinylethyl}-1,2-benzisothiazole-3-carboxamide;
h. N-{2-[1-(3,4-dichlorobenzyl)]-4-piperazinylethyl}-1,2-benzisothiazole-3-carboxamide;
i. N-{2-[1-(2-hydroxybenzyl)]-4-piperazinylethyl}-1,2-benzisothiazole-3-carboxamide;
j. N-{2-[1-(4-trifluoromethylbenzyl]-4-piperizinylethyl}-1,2-benzisothiazole-3-carboxamide;
k. N-{4-[1-(2-methoxyphenyl)-4-piperazinyl)-2-butenyl]-1,2-benzisothiazole-3-carboxamide;
l. N-[3-(1-(1,2-benzisothiazol-3-yl)-4-piperazinyl)propyl]-1,2-benzisothiazole-3-carboxamide; and
m. N-Methyl-N-[2-(benzo[b]thiophen-3-yl)-4-piperazinyl)ethyl]-1,2-benzisoxazole-3-carboxamide.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

N-Methyl-N-[4-(1-(4-fluorobenzoyl)-4-piperidinyl)-butyl]-1,2-benzisothiazole-3-carboxamide hydrochloride A mixture of N-methyl-N-(4-bromobutyl)-1,2-benzisothiazole-3-carboxamide (5.12 g), 4-fluorobenzoyl-piperidine (3.75 g), potassium carbonate (6.77 g), sodium iodide (0.350 g), and dimethylformamide (75 ml) was heated at 70° C. for 17 hr under nitrogen. The reaction mixture was diluted with water (300 ml) and 5% sodium hydroxide solution (20 ml) and extracted with ether. The combined extracts were washed with water, brine, dried over anhydrous sodium sulfate, filtered, and the filtrate was evaporated under reduced pressure. The residue was purified by chromatography on silica gel, using 5–10% methanol in dichloromethane as the eluant. The appropriate fractions were collected and evaporated. The hydrochloride salt was prepared by treating the residue with ethanolic hydrogen chloride. Recrystallization from dichloromethane/ethyl acetate gave 3.15 g (45.9%) of product, mp 148°–150° C. dec.

Analysis: Calculated for $C_{25}H_{29}ClFN_3O_2S$: 61.28% C; 5.96% H; 8.57% N. Found: 61.22% C; 5.98% H; 8.54% N.

EXAMPLE 2

N-[2-(1-(6-Chloro-1,2-benzisoxazol-3-yl)-4-piperidinyl)ethyl]-1,2-benzisothiazole-3-carboxamide A mixture of N-(2-chloroethyl)-1,2-benzisothiazole-3-carboxamide (2.9 g) and 1-(6-chloro-1,2-benzisoxazol-3-yl)piperidine (3.48 g) in dry N-methylpyrrolidinone (125 ml) was heated to 180° C., with stirring, under nitrogen. After 5 hr, the reaction mixture was allowed to cool to room temperature, diluted with water, basified with saturated aqueous sodium carbonate solution, and extracted with ethyl acetate. The organic phase was washed with water, dried over anhydrous magnesium sulfate, filtered, and the filtrate was concentrated in vacuo. The residue was chromatographed on silica using ether as the eluent. The appropriate fractions were collected and evaporated. The residue was triturated with dichloromethane/ether to give 2.38 g (44.6%) of product, mp 132°–134° C.

Analysis: Calculated for $C_{22}H_{21}ClN_4O_2S$: 59.93% C; 4.80% H; 12.71% N. Found: 59.98% C; 4.91% H; 12.65% N.

EXAMPLE 3

N-[3-(1-(6-Chloro-1,2-benzisoxazol-3-yl)-4-piperidinyl)-propyl]-1,2-benzisothiazole-3-carboxamide hydrochloride A mixture of N-(3-chloropropyl)-1,2-benzisothiazole-3-carboxamide (5.0 g), 1-(6-chloro-1,2-benzisoxazol-3-yl)piperidine hydrochloride (5.40 g), potassium carbonate (5.40 g), and sodium iodide (100 mg) in dry N-methylpyrrolidinone (100 ml), was heated to 180° C., with stirring, under nitrogen. After 36 hr, the reaction mixture was allowed to cool to room temperature and partitioned between ethyl acetate/water. The organic phase was washed with water, dried over anhydrous magnesium sulfate, filtered, and the filtrate concentrated in vacuo. The residue was chromatographed on silica using ethyl acetate as the eluent. The appropriate fractions were collected and concentrated. The filtrate was treated with hydrogen chloride in ether. The salt was recrystallized from methanol/dichloromethane/ether to provide 2.87 g (29.4%) of product, mp 221°–223° C.

Analysis: Calculated for $C_{23}H_{24}Cl_2N_4O_2S$: 56.21% C; 4.92% H; 11.40% N. Found: 55.85% C; 4.95% H; 11.19% N.

EXAMPLE 4

N-Methyl-N-[4-(1-(6-fluoro-1,2-benzisoxazol-3-yl)-4-piperidinyl)butyl]-1,2-benzisothiazole-3-carboxamide hydrochloride A mixture of N-methyl-N-(4-bromobutyl)-1,2-benzisothiazole-3-carboxamide (4.84 g), 1-(6-fluoro-1,2-benzisoxazol-3-yl)piperidine (3.15 g), potassium carbonate (4.50 g), sodium iodide (0.560 g), and acetonitrile (200 ml) was heated at 75° C. for 21 hr under nitrogen. The reaction mixture was filtered, the filtercake washed with dichloromethane, and the filtrate concentrated under reduced pressure. The residue was taken up in dichloromethane, washed with 5% sodium hydroxide solution, water, dried over anhydrous sodium sulfate, filtered, and the filtrate was evaporated under reduced pressure. The residue was purified by chromatography on silica gel, using 5–10% methanol in dichloromethane as the eluent. The appropriate fractions were collected and concentrated. The residue was treated with ethanolic hydrogen chloride. Recrystallization from dichloromethane/ethyl acetate gave 2.60 g (39.7%) of product, mp 204°–205° C. dec.

Analysis: Calculated for $C_{25}H_{28}ClFN_4O_2S$: 59.69% C; 5.61% H; 11.14% N. Found: 59.37% C; 5.57% H; 11.06% N.

EXAMPLE 5

N-[2-(1-(4-(2-Oxo-1-benzimidazolinyl)piperidinyl)ethyl]-1,2-benzisothiazole-3-carboxamide A mixture of 1,2-benzisothiazole-3-[N-(2-chloroethyl]carboxamide (5.0 g) and 4-(2-oxo-1-benzimidazolinyl)piperidine (5.87 g) in 1-methyl-2-pyrrolidinone (150 ml) was heated to 180° C., with stirring, under nitrogen. After 18 hr, the reaction mixture was cooled to room temperature and poured into water. The aqueous phase was extracted with ethyl acetate. The combined organic extracts were washed with water, dried over anhydrous magnesium sulfate, filtered, and the filtrate was concentrated in vacuo. The residue was recrystallized from ethyl acetate to provide 4.03 g (46.0%) of product, mp 174°–177° C.

Analysis: Calculated for $C_{17}H_{14}N_4O_2S$: 62.69% C; 5.50% H; 16.61% N. Found: 62.54% C; 5.43% H; 16.39% N.

EXAMPLE 6

N-[2-(1-Methyl)-4-piperazinyl)ethyl]-1,2-benzisothiazole-3-carboxamide dihydrochloride A mixture of N-(2-chloroethyl)-1,2-benzisothiazole-3-carboxamide (3.9 g) and 1-methylpiperazine (3.6 ml) in dry N-methylpyrrolidinone (150 ml) was heated to 180° C., with stirring, under nitrogen. After 18 hr, the reaction mixture was allowed to cool to room temperature, diluted with water, and extracted with ethyl acetate. The organic phase was washed with water, dried over anhydrous magnesium sulfate, filtered, and the filtrate was collected and concentrated in vacuo. The residue was chromatographed on silica using 1:1 methanol/ethyl acetate as the eluent. The appropriate fractions were collected and concentrated. The residue was taken up in ether, and ethereal hydrogen chloride was added. Recrystallization of the precipitate from methanol/dichloromethane/ethyl acetate provided 2.33 g (37.9%) of the salt, mp 227°–230° C.

Analysis: Calculated for $C_{15}H_{22}Cl_2N_4OS$: 47.75% C; 5.88% H; 14.85% N. Found: 47.86% C; 5.95% H; 14.80% N.

EXAMPLE 7

N-[2-(1-Benzyl)-4-piperazinyl)ethyl-1,2-benzisothiazole-3-carboxamide dihydrochloride hemihydrate A mixture of N-(2-chloroethyl)-1,2-benzisothiazole-3-carboxamide (3.0 g) and 1-benzylpiperazine (2.6 ml) in dry N-methylpyrrolidinone (100 ml) was heated to 180° C., with stirring, under nitrogen. After 5 hr, the reaction mixture was allowed to cool to room temperature, diluted with water, basified with saturated aqueous sodium carbonate solution, and extracted with ethyl acetate. The organic phase was washed with water, dried over anhydrous magnesium sulfate, filtered, and the filtrate was concentrated in vacuo. The residue was chromatographed on silica using ethyl acetate as the eluent. The appropriate fractions were collected and evaporated. The residue was dissolved in ether and hydrogen chloride in ether was added. The precipitate was recrystallized from methanol/dichloromethane/ether to provide 2.36 g (40.9%) of product, mp 207°–210° C.

Analysis: Calculated for $C_{21}H_{27}Cl_2N_4O_{1.5}S$: 54.53% C; 5.88% H; 12.11% N. Found: 54.86% C; 5.69% H; 12.36% N.

EXAMPLE 8

N-[2-(1-(2-Methoxyphenyl)-4-piperazinyl)ethyl]-1,2-benzisothiazole-3-carboxamide dihydrochloride A mixture of 1,2-benzisothiazole-3-[N-(2-chloroethyl)]carboxamide (2.24 g) and 1-(2-methoxyphenyl)piperazine (1.8 g) in dry 1-methyl-2-pyrrolidinone (100 ml) was heated with stirring to 120° C., under nitrogen. After 24 hr, the reaction mixture was cooled to room temperature, poured into saturated aqueous sodium carbonate solution, and extracted with ether. The organic extracts were combined, dried over anhydrous magnesium sulfate, filtered, and the filtrate was concentrated in vacuo. The residue was chromatographed on silica using ether as the eluent. The appropriate fractions were combined and concentrated. The reside was taken up in ether and hydrogen chloride in other was added. The precipitate was recrystallized from ether/dichloromethane to provide 1.34 g (30.6%) of product, mp 205°–208° C.

Analysis: Calculated for $C_{21}H_{24}N_4O_2S \cdot 2HCl$: 53.73% C; 5.58% H; 11.93% N. Found: 53.52% C; 5.35% H; 11.73% N.

EXAMPLE 9

N-[2-(1-(3-Chlorophenyl)-4-piperazinyl)ethyl]-1,2-benzisothiazole-3-carboxamide

A mixture of 1,2-benzisothiazole-3-[N-(2-chloroethyl)]carboxamide (4.23 g) and 1-(3-chlorophenyl)piperazine (4.15 g) in dry 1-methyl-2-pyrrolidinone (125 ml) was heated to 180° C., with stirring, under nitrogen. After 18 hr, the reaction mixture was cooled to room temperature and poured into saturated aqueous sodium carbonate solution. The aqueous phase was extracted with ether, and the combined organic extracts were washed with water, dried over anhydrous magnesium sulfate, filtered, and the filtrate was concentrated in vacuo. The residue was chromatographed on silica using ether as the eluent. The appropriate fractions were collected and concentrated. The residue solidified. Recrystallization from ether/dichloromethane provided 2.62 g (37.2%) of product, mp 115°–117° C.

Analysis: Calculated for $C_{20}H_{21}ClN_4OS$: 59.92% C; 5.28% H; 13.97% N. Found: 59.84% C; 5.15% H; 13.93% N.

EXAMPLE 10

N-[3-(1(2-Methoxyphenyl)-4-piperazinyl)propyl]-1,2-benzisothiazole-3-carboxamide dihydrochloride A mixture of N-(3-chloropropyl)-1,2-benzisothiazole-3-carboxamide (4.2 g), 1-(2-methoxyphenyl)piperazine (3.3 g), potassium carbonate (4.55 g), and sodium iodide (100 mg) in dry N-methylpyrrolidinone (150 ml) was heated to 180° C., with stirring, under nitrogen. After 24 hr, the reaction mixture was allowed to cool to room temperature and partitioned between ether/water. The organic phase was dried over anhydrous magnesium sulfate, filtered, and the filtrate was concentrated in vacuo. The residue was chromatographed on silica using ether as the eluent. The appropriate fractions were collected and evaporated. The residue was taken up in ether and hydrogen chloride in ether was added. Recrystallization of the precipitate from methanol/dichloromethane/ether provided 2.12 g (26.6%) of product, mp 191°-194° C.

Analysis: Calculated for $C_{22}H_{28}Cl_2N_4O_2S$: 54.66% C; 5.84% H; 11.59% N. Found: 54.60% C; 5.75% H; 11.51% N.

EXAMPLE 11

N-Methyl-N-[3-(1-(2-methoxyphenyl)-4-piperazinyl)propyl]-1,2-benzisothiazole-3-carboxamide dihydrochloride A mixture of N-methyl-N-(3-bromopropyl)-1,2-benzisothiazole-3-carboxamide (3.4 g), 1-(2-methoxyphenyl)piperazine (2.09 g), potassium carbonate (3.0 g), and sodium iodide (100 mg) in dry acetonitrile (125 ml) was heated to 80° C., with stirring, under nitrogen. After 24 hr, the reaction mixture was allowed to cool to room temperature and evaporated in vacuo. The residue was partitioned between ethyl acetate/water. The organic phase dried over anhydrous magnesium sulfate, filtered, and the filtrate was concentrated in vacuo. The residue was chromatographed on silica using ethyl acetate as the eluent. The appropriate fractions were collected and concentrated. The residue was taken up in ether and hydrogen chloride in ether was added. The precipitate was recrystallized from dichloromethane/ethyl acetate/ether to provide 1.62 g (30.0%) of product, mp 166°-169° C.

Analysis:
Calculated for $C_{23}H_{28}N_4O_2S.HCl$: 55.53% C; 6.08% H; 11.26% N. Found: 55.21% C; 5.90% H; 11.16% N

EXAMPLE 12

N-[4-(1-(2-Methoxyphenyl)-4-piperazinyl)butyl]-1,2-benzisothiazole-3-carboxamide dihydrochloride A mixture of 1,2-benzisothiazole-3-carboxylic acid chloride (2.44 g), 1-(2-methoxyphenyl)-4-(4-aminobutyl)piperazine (3.26 g), and triethylamine (6 ml), in sieve-dried toluene (100 ml) was heated to 80° C., with stirring, overnight. After 24 hr, the reaction mixture was cooled to room temperature and poured into water. The organic phase was separated and the aqueous phase was extracted with ether. The ether extracts and toluene phase were combined, dried over anhydrous magnesium sulfate, filtered, and the filtrate was concentrated in vacuo. The residue was chromatographed on silica using ethyl acetate as the eluent. The appropriate fractions were collected and concentrated. The residue was taken up in ether and ethereal hydrogen chloride was added. The precipitate was recrystallized from ethanol/ethyl acetate and dried (0.1 mm mercury, refluxing toluene temperature) to provide 2.13 g (34.6%) of product, mp 174°-178° C.

Analysis: Calculated for $C_{23}H_{28}N_4O_2S.HCl$: 55.53% C; 6.08% H; 11.26% N Found: 55.49% C; 5.80% C; 11.19% N

EXAMPLE 13

N-Methyl-N-[4-(1-(2-methoxyphenyl)-4-piperazinyl)butyl]-1,2-benzisothiazole-3-carboxamide dihydrochloride hemihydrate A mixture of N-methyl-N-(4-bromobutyl)-1,2-benzisothiazole-3-carboxamide (3.42 g), 1-(2-methoxyphenyl)piperazine (2.01 g), potassium carbonate (2.9 g), and sodium iodide (20 mg) in dry acetonitrile (100 ml) was heated to 80° C., with stirring, under nitrogen. After 18 hr, the reaction mixture was allowed to cool to room temperature and evaporated in vacuo. The residue was partitioned between ethyl acetate/water, and the organic phase was dried over anhydrous magnesium sulfate, filtered, and the filtrate was concentrated in vacuo. The residue was taken up in ether. Hydrogen chloride in ether was added. The precipitate was recrystallized from dichloromethane/ether to provide 1.87 g (34.3%) of the product, mp 169°-171° C.

ANALYSIS: Calculated for $C_{24}H_{30}N_4O_2.2HCl.0.5H_2O$: 55.37% C; 6.38% H; 10.76% N. Found: 55.64% C; 6.42% H; 10.75% N.

EXAMPLE 14

N-[2-(1-(1,2-Benzisothiazol-3-yl)-4-piperazinylethyl]-1,2-benzisothiazole-3carboxamide A mixture of 1,2-benzisothiazole-3-[N-(2-chloroethyl)]carboxamide (1.2 g), and 1,2-benzisothiazol-3-ylpiperazine (1.3 g) in 1-methyl-2-pyrrolidinone (25 ml) was heated to 190°, with stirring, under nitrogen. After 2 hr, the reaction mixture was cooled to room temperature and poured into saturated aqueous sodium carbonate solution. The aqueous phase was extracted with ether, and the organic extracts were combined, dried over anhydrous magnesium sulfate, filtered, and the filtrate was concentrated in vacuo. The residue was chromatographed on silica using ether eluent. The appropriate fractions were collected and concentrated. The residual solid was recrystallized from ether to provide 1.33 g (62.8%) of product, mp 160°-163° C.

Analysis: Calculated for $C_{21}H_{21}N_5OS_2$: 59.55% C; 5.00% H; 16.53% N. Found: 59.20% C; 4.99% H; 16.31% N.

EXAMPLE 15

N-[4-(1-(1,2-Benzisothiazol-3-yl)-4-piperazinyl)butyl]-1,2-benzisothiazole-3-carboxamide hydrochloride A mixture of 1,2-benzisothiazole-3-carboxylic acid chloride (2.6 g), 1-(1,2-benzisothiazol-3-yl)-4-(4-aminobutyl)piperazine (3.45 g), and triethylamine (5 ml), in sieve-dried toluene (100 ml) was heated to 80° C., with stirring, overnight. After 24 hr, the reaction mixture was cooled to room temperature and added to water. The organic phase was separated and the aqueous phase was extracted with ethyl acetate. The ethyl acetate extracts and the toluene phase were combined and dried anhydrous over magnesium sulfate. The organic phase was filtered and the filtrate concentrated in vacuo. The residue was chromatographed on silica using ethyl acetate. The appropriate fractions were collected and concentrated in vacuo. The residue was taken up in ether and hydrogen chloride in ether was added. The precipitate was recrystallized from dichloromethane/ether and dried (0.1 mm mercury, refluxing isopropanol alcohol temperature) to provide 1.60 g (27.1%) of product, mp 203°–205° C.

Analysis: Calculated for $C_{23}H_{23}N_5OS_2HCl\cdot0.5H_2O$: 55.57% C; 5.47% H; 14.09% N. Found: 55.32% C; 5.20% H; 13.86% N.

EXAMPLE 16

N-Methyl-N-[4-(1-(6-fluorobenzo[b]thiophen-3-yl)-4-piperazinyl)butyl]-1,2-benzisothiazol-3-carboxamide hydrochloride A mixture of N-methyl-N-(4-bromobutyl)-1,2-benzisothiazol-3-carboxamide (4.0 g), 6-fluoro-3-piperazinylbenzo[b]thiophene (4.0 g), potassium carbonate (5.0 g), sodium iodide (350 mg), and acetonitrile (200 ml) was heated under reflux, under nitrogen. After 16 hr, the reaction mixture was filtered, the filtercake washed with dichloromethane, and the filtrate concentrated under reduced pressure. The residue was taken up in dichloromethane, washed with 5% sodium hydroxide solution, water, dried over anhydrous sodium sulfate, filtered, and the filtrate was concentrated. The residue was chromatographed on silica gel, eluting with 7.5% methanol in dichloromethane. The appropriate fractions were collected and concentrated. Ethereal hydrogen chloride was added to the residue. Recrystallization of the precipitate from dichloromethane/ethyl acetate afforded 2.80 g (44.2%) of product, mp 183°–185° C.

Analysis: Calculated for $C_{25}H_{28}ClFN_4OS_2$: 57.85% C; 5.44% H; 10.79% N. Found: 57.66% C; 5.21% H; 10.61% N.

EXAMPLE 17

N-Methyl-N-[4-(1-(1,2-benzisothiazol-3-yl)-4-piperazinyl)butyl]-1,2-benzisothiazole-3-carboxamide hydrochloride A mixture of N-methyl-N-(4-bromobutyl)-1,2-benzisothazole-3-carboxamide (4.0 g), 1-(1,2-benzisothiazole-3-yl)piperazine hydrochloride (3.13 g), potassium carbonate (5.10 g), and sodium iodide (20 mg) in dry acetonitrile (100 ml) was heated to 80° C., with stirring, under nitrogen. After 18 hr, the reaction mixture was allowed to cool to room temperature and concentrated in vacuo. The residue was partitioned between ethyl acetate/water, and the organic phase was dried over anhydrous magnesium sulfate, filtered, and the filtrate was concentrated in vacuo. The residue was chromatographed on silica using 10% methanol/90% ethyl acetate as the eluent. The appropriate fractions were collected and evaporated. The residue was taken up in ether. Ethereal hydrogen chloride was added. Recrystallization from dichloromethane/ether provided 3.36 g (55.7%) of product, mp 210°–211° C.

ANALYSIS: Calculated for $C_{24}H_{28}ClN_5OS_2$: 57.41% C; 5.62% H; 13.95% N. Found: 57.22C; 5.49% H; 13.83% N.

EXAMPLE 18

N-[4-(1-(2-Methoxyphenyl)-4-piperazinyl)-2-butynyl]-1,2-benzisothiazole-3-carboxamide dihydrochloride A mixture of 1,2-benzisothiazole-3-carboxylic acid chloride (2.0 g) and 1-(2-methoxyphenyl)-4-(4-amino-2-butynyl)piperazine (2.63 g) in dichloromethane (100 ml), was stirred while triethylamine (2.83 ml) was added dropwise. Stirring was continued overnight. After 24 hr, the reaction mixture was diluted with water and extracted with dichloromethane. The organic phase was dried over anhydrous magnesium sulfate, filtered, and the filtrate was concentrated in vacuo. The residue was chromatographed on silica using ethyl acetate as the eluent. The appropriate fractions were collected and concentrated. The residue was taken up in ether/dichloromethane. Ethereal hydrogen chloride was added. The precipitate was recrystallized from methanol/dichloromethane/ether to provide 2.27 g (45.7%) of product, mp 162°–164° C.

ANALYSIS: Calculated for $C_{23}H_{26}Cl_2N_4O_2S$: 55.98% C; 5.31% H; 11.35% N. Found: 55.84% C; 5.06% H; 11.25% N.

EXAMPLE 19

Z-N-[4-(1-(2-Methoxyphenyl)-4-piperazinyl)-2-butenyl]-1,2-benzisothiazole-3-carboxamide dihydrochloride A mixture of 1,2-benzisothiazole-3-carboxylic acid chloride (1.77 g) and Z-1-(2-methoxyphenyl)-4-(4-amino-2-butenyl)piperazine (2.34 g) in dichloromethane (100 ml) was stirred while triethylamine (2.51 ml) was added dropwise. Stirring was continued overnight. After 24 hr, the reaction mixture was diluted with water and saturated aqueous sodium carbonate solution and extracted with dichloromethane. The organic phase was washed with water, dried over anhydrous magnesium sulfate, filtered, and the filtrate was concentrated in vacuo. The residue was taken up in dichloromethane/ether and hydrogen chloride in ether was added. The precipitate was recrystallized from methanol/dichloromethane/ether to provide 2.31 g (51.7%) of product, mp 184–187.

ANALYSIS: Calculated for $C_{23}H_{28}Cl_2N_4O_2S$: 55.76% C; 5.70% H; 11.31% N. Found: 55.52% C; 5.65% H; 11.21% N.

EXAMPLE 20

N-[4-(1-(2-Pyrimidyl)-4-piperazinyl-2-butynyl]-1,2-benzisothiazole-3-carboxamide A mixture of 1,2-benzisothiazole-3-carboxylic acid chloride (2.55 g) and 1-(2-pyrimidyl)-4-(4-amino-2-butynyl)piperazine (3.0 g) in dichloromethane (100 ml) was stirred while triethylamine (3.62 ml) was added dropwise. Stirring was continued overnight. After 24 hr, the reaction mixture was diluted with water, dried over magnesium sulfate, filtered, and the filtrate was concentrated in vacuo. The resiude was recrystallized from dichloromethane/ether/hexane to provide 3.67 g (72.3%) of product, mp 102°–104° C.

Analysis: Calculated for $C_{20}H_{20}N_6OS$: 61.21% C; 5.14% H; 21.41% N. Found: 61.10% C; 4.92% H; 21.25% N.

EXAMPLE 21

N-Methyl-N-[4-(1-(6-fluorobenzo[b]thiophen-3-yl)-4-piperazinyl)butyl]-1,2-benzisoxazole-3-carboxamide hydrochloride A mixture of N-methyl-N-(4-bromobutyl)-1,2-benzisoxazole-3-carboxamide (4.22 g), 1-(6-fluorobenzo[b]thiophen-3-yl)piperazine (3.89 g), potassium carbonate (5.00 g), sodium iodide (0.80 g), and acetonitrile (200 ml) was heated at 75° C. for 17 hr, under nitrogen.

The reaction mixture was filtered, the filtercake was washed with dichloromethane, and the filtrate was evaporated. The residue was taken up in dichloromethane, washed with 5% sodium hydroxide solution, water, dried over anhydrous sodium sulfate, filtered, and the filtrate was evaporated under reduced pressure. The residue was purified by chromatography on silica gel, using 7.5% methanol in ethyl acetate as the eluant. The appropriate fractions were collected and evaporated. Ethanolic hydrogen chloride was added. Recrystallization of the precipitate from ethanol/ethyl acetate gave 2.11 g (30.8%) of product, mp 145°-147° C.

Analysis: Calculated for $C_{25}H_{28}ClFN_4O_2S$: 59.69% C; 5.61% H; 11.14% N. Found: 59.72% C; 5.72% H; 11.15% N.

EXAMPLE 22

N-[2-(1-(2-Methoxyphenyl)-4-piperazinyl)ethyl]-1,2-benzisothiazole-3-carboxamide A mixture of N-(2-chloroethyl)-1,2-benzisoxazole-3-carboxamide (4.00 g), N-(2-methoxyphenyl)piperazine (4.15 g), and N-methylpyrrolidinone (100 ml) was heated at 170° C. for 4.5 hr. The reaction mixture was allowed to cool, diluted with 5% sodium hydroxide solution (400 ml), and the aqueous mixture was extracted with ethyl acetate. The combined extracts were washed with water, brine, dried over anhydrous magnesium sulfate, and filtered. The filtrate was concentrated in vacuo. The residue was chromatographed on silica gel using 5% methanol in dichloromethane. The appropriate fractions were collected and concentrated. Recrystallization of the residue from ether/hexanes gave 2.22 g (32.8%) of product, mp 107°-110° C.

Analysis Calculated for $C_{21}H_{24}N_4O_3$: 66.30% C; 6.36% H; 14.73% N. Found 66.38% C; 6.22% H; 14.72% N.

EXAMPLE 23

N-[2-(1-(6-fluorobenzo[b]thiophen-3-yl)-4-piperazinyl)ethyl]-1,2-benzisoxazole-3-carboxamide hydrochloride A mixture of N-(2-chloroethyl)-1,2-benzisoxazole-3-carboxamide (4.40 g), 6-fluoro-3-(1-piperazinyl)benzo[b]thiophene (5.90 g), and N-methylpyrrolidinone (100 ml) was heated at 160° C. for 3.0 hr. The reaction mixture was allowed to cool, diluted with water (350 ml), basified with 25% sodium hydroxide to pH-8, and extracted with ether. The combined extracts were washed with water, brine, dried over anhydrous magnesium sulfate, and filtered. The filtrate was concentrated in vacuo. The residue was chromatographed on silica gel, using 75% ethyl acetate in hexanes as the eluant. The appropriate fractions were collected and concentrated. Ethanolic hydrogen chloride was added to the residue. Recrystallization of the precipitate from methanol/ethanol gave 2.13 g (23.6%) of product, mp 225°-228° C. dec.

Analysis:
Calculated for $C_{22}H_{22}ClFN_4O_2S$: 57.32% C; 4.81% H; 12.15% N. Found: 57.24% C; 4.45% H; 12.07% N.

EXAMPLE 24

N-[2-(1-(4-Fluorobenzoyl)-4-piperidinyl)ethyl]-1,2-benzisothiazole-3-carboxamide hydrochloride hemihydrate A mixture of N-(2-chloroethyl)-1,2-benzisothiazole-3-carboxamide (3.5 g) and 1-(4-fluorobenzoyl)piperidine (3.63 g) in dry 1-methyl-2-pyrrolidinone (125 ml) was heated with stirring to 180° C., under nitrogen. After 3 hr, the reaction mixture was cooled to room temperature and poured into saturated aqueous sodium carbonate solution. The aqueous phase was extracted with ethyl acetate, and the combined organic extracts were washed with water, dried over anhydrous magnesium sulfate, filtered, and the filtrate was concentrated in vacuo. The residue was triturated with ether, and the filtrate was concentrated. The residue was chromatographed on silica using ethyl acetate as the eluent. The appropriate fractions were combined and concentrated. The residue was taken up in ether and hydrogen chloride in ether was added. The precipitate was recrystallized from methanol/dichloromethane/ether to provide 1.21 g (18.1%) of product, mp 188°-190° C.

Analysis: Calculated for $C_{22}H_{24}ClFN_3O_{2.5}S$: 57.82% C; 5.29% H; 9.19% N. Found: 57.73% C; 5.06% H; 9.09% N.

EXAMPLE 25

N-Methyl-N-(4-bromobutyl)-1,2-benzisoxazole-3-carboxamide

To a suspension of sodium hydride (1.09 g, 60% dispersion-in-oil) and dimethylformamide (10 ml), cooled in an ice bath, was added a solution of N-methyl-1,2-benzisothiazole-3-carboxamide (4.38 g) and dimethylformamide (10 ml), with stirring, at a rate such as to maintain gentle evolution of hydrogen. After the addition was complete, the reaction mixture was stirred at ice bath temperature for 10 mins. The ice bath was removed and the mixture was added dropwise to a solution 1,4-dibromobutane (7.8 ml) and dimethylformamide (10 ml), with stirring. The mixture was stirred at ambient temperature overnight, and water (250 ml) was added. The mixture was extracted with ether, and the combined extracts were washed with water, saturated sodium chloride solution, dried over anhydrous sodium sulfate, and filtered. The filtrate was concentrated, and the residue was chromatographed on silica gel (500 g). The column was eluted with 5%-ethyl acetate:dichloromethane. The appropriate fractions were collected and evaporated to give 4.28 g (55%) of product, as an oil.

EXAMPLE 26

6-Fluoro-3-(1-piperazinyl)benzo[b]thiophene maleate

A mixture of methyl-6-fluoro-3-aminobenzo[b]thiophene-2-carboxylate (20.1 g), 1-methylpiperazine (13.1 g), and 1-methyl-2-pyrrolidinone (100 ml) was heated at 176° C. for 2 hrs, under nitrogen. The solution was diluted with water (400 ml) and extracted with ether. The combined extracts were washed with water, brine, dried over anhydrous sodium sulfate, filtered, and the filtrate was concentrated under reduced pressure to give 9.32 g of 3-amino-6-fluorobenzo[b]thiophene.

A mixture of 3-amino-6-fluorobenzo[b]thiophene (9.32 g), piperazine (15.0 g), and 1-methyl-2-pyrrolidinone (100 ml), was heated 186° to 192° C., for 14 hrs, under nitrogen. The mixture was cooled, diluted with water (500 ml), and extracted with ether. The combined extracts were washed with water, brine, dried over anhydrous potassium carbonate, filtered, and the filtrate was concentrated under reduced pressure. The residue was chromatographed on silica gel (eluting with 30% methanol in dichloromethane) to give 3.03 g of the free base, as an oil.

A solution of maleic acid (1.49 g) in 2-propanol (20 ml) was added to a solution of the free base (3.03 g) and 2-propanol (20 ml). The mixture was concentrated under reduced pressure, and the residue was recrystallized from methanol/ethyl acetate to afford 2.72 g (8.80%) of product, mp 173°–175° C.

Analysis: Calculated for $C_{16}H_{17}FN_2O_4S$: 54.54% C; 4.86% H; 7.95% N. Found: 54.53% C; 4.69% H; 8.01% N.

EXAMPLE 27

N-(1-Methylethyl)-N-(2-hydroxyethyl)-1,2-benzisoxazole-3-carboxamide

A mixture of ethyl-1,2-benzisoxazole-3-carboxylate (10.0 g), 2-(1-methylethylamino)ethanol (16.1 g) and toluene (80 ml) was heated to 140° C. in a bomb for 4 hrs. The solution was diluted with ether (50 ml), washed with 5% sodium bicarbonate solution, water, brine, dried over anhydrous sodium sulfate, and concentrated under reduced pressure. The residue was chromatographed on silica gel, eluting with 60% ethyl acetate in hexanes to give 10.6 g (81.4%) of product. Recrystallization from dichloromethane/hexanes afforded the analytical sample, mp 92°–94° C.

Analysis: Calculated For $C_{13}H_{16}N_2O_3$: 62.89% C; 6.50% H; 11.28% N. Found: 63.00% C; 6.51% H; 11.24% N.

EXAMPLE 28

-N-Methyl-N-[2-(1-(6-fluoro-1,2-benzisoxazol-3-yl)-4-piperidinyl)ethyl]-1,2-benzisothiazole-3-carboxamide hydrochloride hemihydrate To a mixture of N-methyl-N-(2-hydroxyethyl)-1,2-benzisothiazole-3-carboxamide (4.00 g) and triethylamine (2.48 ml), in sieve-dried toluene (100 ml) stirred at 0°, under nitrogen, was added dropwise methanesulfonyl chloride (1.34 ml). The mixture was stirred and warmed to ambient temperature. After 45 mins, 4-(6-fluoro-1,2-benzisoxazol-3-yl)piperidine (3.72 g) was added, and the mixture was heated for 18 hrs under reflux, with stirring. The mixture was allowed to cool to room temperature, and was added to 2% sodium hydroxide solution. The organic layer was separated, and the aqueous layer was extracted with ethyl acetate. The combined extracts were washed with water, dried over anhydrous magnesium sulfate, filtered, and the filtrate was concentrated in vacuo. The residue was chromatographed on silica using ethyl acetate as eluent. The appropriate fractions were collected and evaporated. The residue was dissolved in dichloromethane and hydrogen chloride in ethanol was added, followed by ether. The salt was recrystallized from dichloromethane/ether to provide 1.45 g (14.0%) product, mp 211°–214° C. (dec).

Analysis: Calculated for $C_{23}H_{23}N_4O_2S.HCl.0.5H_2O$: 57.07% C; 5.21% H; 11.58% N. Found: 57.04% C; 5.08% H; 11.52% N.

EXAMPLE 29

N-Methyl-N-[2-(1-(4-fluorobenzoyl)-4-piperidinyl)ethyl]-1,2-benzisothiazole-3-carboxamide hydrochloride hemihydrate To a mixture of N-methyl-N-(2-hydroxyethyl)-1,2-benzisothiazole-3-carboxamide (3.43 g) and triethylamine (2.13 ml) in sieve-dried toluene (100 ml) methanesulfonyl chloride (1.15 ml) was added dropwise at 0°, under nitrogen, and the mixture was allowed to warm to room temperature, with stirring. After 45 mins, 1-(4-fluorobenzoyl)piperidine (3.01 g) was added, and the mixture heated under reflux for 18 hrs, with stirring. The mixture was allowed to cool to room temperature and was added to 5% aqueous sodium bicarbonate solution. The organic layer was separated, and the aqueous layer was extracted with ethyl acetate. The combined organic fractions were washed with water, dried over magnesium sulfate, and filtered. The filtrate was concentrated in vacuo, and the residue was chromatographed on silica using ethyl acetate as the eluent. The appropriate fractions were collected and concentrated. The residue was dissolved in dichloromethane and hydrogen chloride in ethanol, followed by ether was added. The salt was recrystallized from dichloromethane/ethyl acetate to provide 1.54 g (22.6%) of product, mp 214°–217° C. (dec.).

Analysis: Calculated for $C_{23}H_{24}FN_3O_2S.HCl.0.5H_2O$: 58.65% C; 5.56% H; 8.92% N. Found: 58.28% C; 5.68% H; 8.78% N.

EXAMPLE 30

N-Methyl-N-[2-(1-(4-fluorobenzoyl)-4-piperidinyl)ethyl]-1,2-benzisoxazole-3-carboxamide hydrochloride To solution of N-methyl-N-(2-hydroxyethyl)-1,2-benzisoxazole-3-carboxamide (4.98 g), triethylamine (2.36 g), and toluene (55 ml) at 0° C., was added methanesulfonyl chloride (2.60 g). The mixture was stirred at 0° C. for 25 mins. To the mixture, 4-(4-fluorobenzoyl)piperidine hydrochloride (6.48 g) and triethylamine (6.46 g) was added, and the reaction mixture was heated under reflux for 13 hrs. The mixture was filtered, and the filtrate was concentrated under reduced pressure. The residue was dissolved in dichloromethane (225 ml), washed with 10% sodium hydroxide solution, water, dried over anhydrous sodium sulfate, and filtered. The filtrate was concentrated under reduced pressure. The residue was chromatographed on silica gel, eluting with 0–10% ethanol in ethyl acetate. The appropriate fractions were collected and concentrated to afford 3.74 g of product as the free base. The free base was converted into its hydrochloride with ethanolic-hydrogen chloride. Recrystallization from methanol/ethyl acetate gave 2.24 g (22.2%) of product, mp 218–221° C. (dec).

Analysis: Calculated for $C_{23}H_{25}ClFN_3O_3$: 61.95% C; 5.65% H; 9.42% N. Found: 61.82% C; 5.57% H; 9.37% N.

EXAMPLE 31

N-(1-Methylethyl)-N-[2-(1-(6-fluoro-1,2-benzisoxazol-3-yl)-4-piperadinyl)ethyl]-1,2-benzisoxazol-3-carboxamide Under a nitrogen atmosphere, methanesulfonyl chloride (3.70 g) was rapidly added to a solution of N-(1-methylethyl)-N-(2-hydroxyethyl)-1,2-benzisoxazole-3-carboxamide (8.00 g), triethylamine (3.27 g), and tetrahydrofuran (150 ml), at 0° C., and the mixture stirred at 0° C. for 30 mins. To the mixture was added rapidly a suspension of 4-(6-fluoro-1,2-benzisoxazol-3-yl)piperidine (7.80 g), triethylamine (6.53 g), and tetrahydrofuran (60 ml), and the mixture was heated under reflux for 12 hrs. Water was added and the solution was concentrated under reduced pressure. The residue was dissolved in dichloromethane (150 ml), washed with 10% sodium hydroxide solution, water, dried over anhydrous sodium sulfate, and filtered. The filtrate was concentrated under reduced pressure. The residue was chromatographed on silica gel, eluting with 80% ethyl acetate in hexanes. The appropriate fractions were collected and evaporated, and the residue was recrystallized from ether to afford 2.33 g (16.0%) of product, mp 118°-120° C.

ANALYSIS:

Calculated for $C_{25}H_{27}FN_4O_3$: 66.65% C; 6.04% H; 12.44% N.

Found: 66.63% C; 6.04% H; 12.41% N.

EXAMPLE 32

N-Methyl-N-[2-(1-(6-fluoro-1,2-benzisoxazol-3-yl)-4-piperidinyl)ethyl]-1,2-benzisoxazole-3-carboxamide Under a nitrogen atmosphere, methanesulfonyl chloride (3.70 g) was rapidly added to a solution of N-methyl-N-(2-hydroxyethyl)-1,2-benzisoxazole-3-carboxamide (7.10 g), triethylamine (3.27 g), and tetrahydrofuran (100 ml) at 0° C., and the mixture was stirred at 0° C. for 60 mins. To the mixture was rapidly added a suspension of 4-(6-fluoro-1,2-benzisoxazol-3-yl)piperidine (8.10 g), triethylamine (7.26 g), and tetrahydrofuran (80 ml), and the mixture was heated under reflux for 16 hrs. Water was added, and the solution was concentrated under reduced pressure. The residue was diluted with 10% sodium hydroxide solution and extracted with 50% ether-toluene. The combined extracts were washed with water and brine, dried over anhydrous potassium carbonate, filtered, and the filtrate was concentrated under reduced pressure. The residue was chromatographed on silica gel eluting with ethyl acetate. The appropriate fractions were collected and evaporated. The residue was recrystallized from ether to afford 3.01 g (22.1%) of product, mp 94°-97° C.

Analysis

Calculated for $C_{23}H_{23}FN_4O_3$: 65.39% C; 5.49% H; 13.26% N.

Found: 65.30% C; 5.51% H; 13.18% N.

EXAMPLE 33

N-(1-Methylethyl)-N-[3-(1-(4-fluorobenzoyl)-4-piperidinyl)propyl]-1,2-benzisoxazole-3-carboxamide hydrochloride hemihydrate To a solution of N-(1-methylethyl)-N-(3-hydroxypropyl)-1,2-benzisoxazole-3-carboxamide (7.80 g), triethylamine (3.05 g), and toluene (200 ml), under a nitrogen atmosphere at 0° C., methanesulfonyl chloride (3.40 g), was added rapidly and the mixture was stirred at 0° C. After 35 mins, 4-(4-fluorobenzoyl)piperidine hydrochloride (7.95 g) and triethylamine (8.71 g) were added, and the mixture was heated under reflux for 16 hrs. The reaction mixture was washed with 10% sodium hydroxide, water, and brine, dried over anhydrous sodium sulfate, filtered, and the filtrate was concentrated. The residue was chromatographed on silica gel, eluting with 5 to 10% methanol in ethyl acetate. The appropriate fractions were collected and evaporated. A solution of the residue in methanol was acidified with hydrogen chloride-ethanol solution and diluted with ether. The mixture was refrigerated, and the solid was collected. Recrystallization of the solid from ethanol/ethyl acetate afforded 1.50 g (10.2%) of product, mp 177°-179° C.

Analysis:

Calculated for $C_{26}H_{31}ClFN_3O_3 \cdot 0.5H_2O$: 62.83% C; 6.49% H; 8.45% N.

Found: 62.86% C; 6.28% H; 8.30% N.

EXAMPLE 34

N-Methyl-N-[3-(1-(4-fluorobenzoyl)piperidinyl)propyl]-1,2-benzisothiazole-3-carboxamide dihydrochloride A mixture of N-methyl-N-(3-chloropropyl)-1,2-benzisothiazole-3-carboxamide (7.13 g), 1-(4-fluorobenzoyl)piperidine (6.44 g), potassium carbonate (7.33 g), and sodium iodide (300 mg) in dry 1-methyl-2-pyrrolidinone (150 ml) was heated to 120° C., with stirring, under nitrogen. After 24 hrs, the mixture was allowed to cool to room temperature and the residue was partitioned between ethyl acetate/water. The organic phase was washed with water, dried over anhydrous magnesium sulfate, filtered, and the filtrate was concentrated in vacuo. The crude residue was chromatographed twice on silica using 10:90 methanol:ethyl acetate as the eluent. The appropriate fractions were collected and evaporated. The residue was dissolved in ether and hydrogen chloride in ethanol was added Recrystallized of the precipitate from dichloromethane/ether gave 0.642 g (5.09%) of produ mp 189°-191° C.

ANALYSIS

Calculated for $C_{24}H_{27}ClFN_3O_2S$: 60.56% C; 5.72% H; 8.83% N.

Found: 60.32% C; 5.75% H; 8.70% N.

EXAMPLE 35

N-Methyl-N-[3-(1-(4-fluorobenzoyl)-4-piperidinyl)propyl]-1,2-benzisoxazole-3-carboxamide A mixture of N-methyl-N-(3-chloropropyl)-1,2-benzisoxazole-3-carboxamide (4.42 g), 4-fluorobenzoyl-piperidine hydrochloride (4.40g), potassium carbonate (8.12 g), sodium iodide (0.400 g), and acetonitrile (250 ml) was heated at 100° C. for 27.5 hrs, under nitrogen. The reaction mixture was filtered, and the filter cake was washed with dichloromethane. The filtrate was concentrated under reduced pressure. The residue was dissolved in dichloromethane, washed with 10% sodium hydroxide, water, dried over anhydrous sodium sulfate, filtered, and the filtrate was concentrated under reduced pressure. The residue was chromatographed on silica gel, using 5% methanol in dichloromethane as the eluent. The appropriate fractions were collected and evaporated. The residue was recrystallized from ethanol/hexane to give 1.55 g (16.2%) of product, mp 85°-87° C. dec.

ANALYSIS:

Calculated for $C_{24}H_{26}FN_3O_3$: 68.07% C; 6.19% H; 9.92% N.

Found: 68.02% C; 6.14% H; 9.89% N.

We claim:

1. A compound of the formula

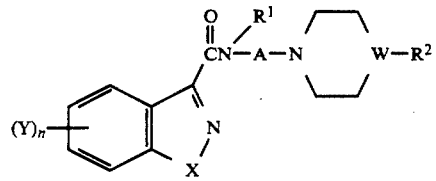

wherein $R^1$ is hydrogen or loweralkyl; $R^2$ is loweralkyl or a group of the formula

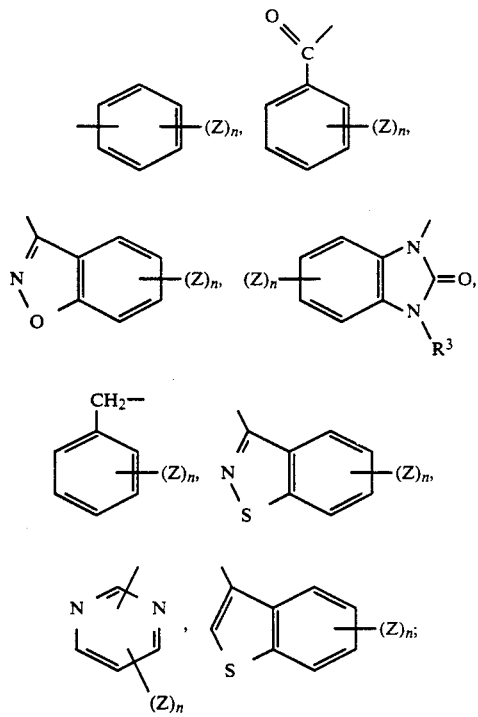

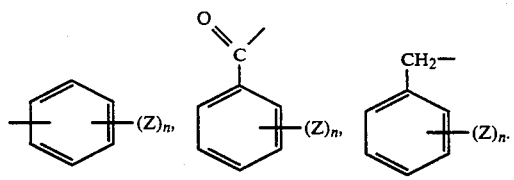

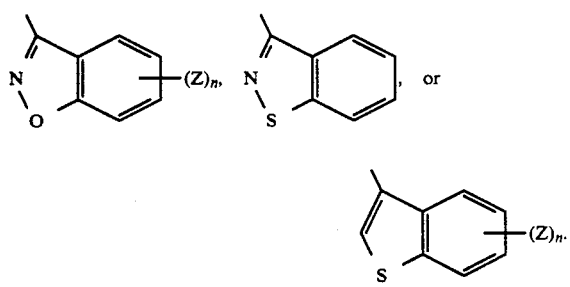

R³ is hydrogen or loweralkyl; A is loweralkylene, a group of the formula —CHR⁴CH═CHCHR⁴—, or —CHR⁴C≡CHR⁴—; R⁴ is hydrogen or loweralkyl; X is O or S; W is CH; Y is hydrogen, loweralkyl, loweralkoxy, hydroxy, halogen, or trifluoromethyl; Z is hydrogen, loweralkyl, loweralkoxy, hydroxy, halogen, or trifluoromethyl; n is 1 or 2 wherein the solid line (—) refers to the point of attachment of the group to the indicated member of the formulas; the geometric and optical isomers thereof, or a pharmaceutically acceptable salt thereof.

2. A compound according to claim 1 wherein R² is a group of the formula

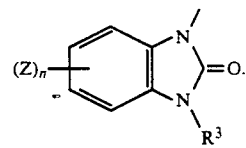

3. A compound according to claim 1 wherein R² is

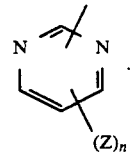

4. A compound according to claim 1 wherein R² is

5. A compound according to claim 1 wherein R² is

6. The compound according to claim 2 which is N-methyl-N-[4-(1-(4-fluorobenzoyl)-4-piperidinyl)butyl]-1,2-benzisothiazole-3-carboxamide.

7. The compound according to claim 3 which is N-[2-(1-(6-chloro-1,2-benzisoxazol-3-yl)-4-piperidinyl)ethyl]-1,2-benzisothiazole-3-carboxamide.

8. The compound according to claim 3 which is N-[3-(1-(6-chloro-1,2-benzisoxazol-3-yl)-4-piperidinyl)-propyl]-1,2-benzisothiazole-3-carboxamide.

9. The compound according to claim 3 which is N-methyl-N-[4-(1-(6-fluoro-1,2-benzisoxazol-3-yl)-4-piperidinyl)butyl]-1,2-benzisothiazole-3-carboxamide.

10. The compound according to claim 4 which is N-[2-(1-(4-(2-oxo-1-benzimidazolinyl)piperidinyl))ethyl]-1,2-benzisothiazole-3-carboxamide.

11. The compound according to claim 2 which is N-[2-(1-(4-fluorobenzoyl)-4-piperidinyl)ethyl]-1,2-benzisothiazole-3-carboxamide.

12. The compound according to claim 3 which is N-methyl-N-[2-(1-(6-fluoro-1,2-benzisoxazol-3-yl)-4-piperidinyl)ethyl]-1,2-benzisothiazole-3-carboxamide.

13. The compound according to claim 2 which is N-methyl-N-[2-(1-(4-fluorobenzoyl)-4-piperidinyl)ethyl]-1,2-benzisothiazole-3-carboxamide.

14. The compound according to claim 2 which is N-methyl-N-[2-(1-(4-fluorobenzoyl)-4-piperidinyl)ethyl]-1,2-benzisoxazole-3-carboxamide.

15. The compound according to claim 2 which is N-(1-methylethyl)-N-[2-(1-(6-fluoro-1,2-benzisoxazol-3-yl)-4-piperidinyl)ethyl]-1,2-benzisoxazole-3-carboxamide.

16. The compound according to claim 3 which is N-methyl-N-[2-(1-(6-fluoro-1,2-benzisoxazol-3-yl)-4-piperidinyl)ethyl]-1,2-benzisoxazole-3-carboxamide.

17. The compound according to claim 2 which is N-(1-methylethyl)-N-[3-(1-(4-fluorobenzoyl)-4-piperidinyl)propyl]-1,2-benzisoxazole-3-carboxamide.

18. The compound according to claim 2 which is N-methyl-N-[3-(1-(4-fluorobenzoyl)-4-piperidinyl)-propyl]-1,2-benzisothiazole-3-carboxamide.

19. The compound according to claim 2 which is N-methyl-N-[3-(1-(4-fluorobenzoyl)-4-piperidinyl)-propyl]-1,2-benzisoxazole-3-carboxamide.

20. A method of treating psychoses which comprises administering to a mammal in need of psychoses treatment, a psychoses treating effective amount of a compound according to claim 1.

21. A psychoses-treating composition comprising an adjuvant and as the effective ingredient, a psychoses-treating effective amount of a compound according to claim 1.

* * * * *

REEXAMINATION CERTIFICATE (2123rd)

United States Patent [19]

Hrib et al.

[11] B1 5,143,923

[45] Certificate Issued Nov. 2, 1993

[54] BENZOISOTHIAZOLE- AND [BENZIOSOX-AZOLE-3-CARBOXAMIDES] BENZIOSOXAZOLE-3-CARBOXAMIDES

[75] Inventors: Nicholas J. Hrib, Somerville; John G. Jurcak, Union City, both of N.J.

[73] Assignee: Hoechst-Roussel Pharmaceuticals Incorporated, Bridgewater, N.J.

Reexamination Request:
No. 90/002,891, Nov. 16, 1992

Reexamination Certificate for:
Patent No.: 5,143,923
Issued: Sep. 1, 1992
Appl. No.: 693,168
Filed: Apr. 29, 1991

[51] Int. Cl.$^5$ .............. A61K 31/445; A61K 31/495; C07D 413/10; C07D 417/10
[52] U.S. Cl. .................. 514/321; 514/254; 514/256; 514/269; 514/322; 514/323; 514/324; 544/295; 544/298; 544/333; 544/368; 546/198; 546/199
[58] Field of Search ............... 544/295, 368; 546/198, 546/199; 514/254, 321, 322

[56] References Cited

U.S. PATENT DOCUMENTS 2,626,260  1/1953  Clinton ................. 548/241

*Primary Examiner*—Cecilia Tsang

[57] ABSTRACT

Novel benzisothiazole- and benzisoxazole-3-carboxamides, processes and intermediates for the preparation thereof, and methods of treating psychoses utilizing compounds and compositions thereof are disclosed.

REEXAMINATION CERTIFICATE ISSUED UNDER 35 U.S.C. 307

THE PATENT IS HEREBY AMENDED AS INDICATED BELOW.

The title of the invention has been changed as follows:
[BENZOISOTHIAZOLE- AND BENZIOSOXAZOLE-3-CARBOXAMIDES] *BENZIOSOXAZOLE-3-CARBOXAMIDES*

AS A RESULT OF REEXAMINATION, IT HAS BEEN DETERMINED THAT:

The patentability of claims 1-21 is confirmed.

* * * * *